United States Patent
Zirkenbach et al.

(10) Patent No.: US 7,300,474 B2
(45) Date of Patent: Nov. 27, 2007

(54) AQUEOUS LIQUID FORMULATIONS OF PYRAZOLINE BRIGHTENERS

(75) Inventors: Gerhard Zirkenbach, Rüdesheim (DE); Alexander Lerch, Geinhausen (DE)

(73) Assignee: Clariant Produkte (Deutschland) GmbH, Sulzbach (DE)

(*) Notice: Subject to any disclaimer, the term of this patent is extended or adjusted under 35 U.S.C. 154(b) by 89 days.

(21) Appl. No.: 10/506,136

(22) PCT Filed: Feb. 20, 2003

(86) PCT No.: PCT/EP03/01730

§ 371 (c)(1),
(2), (4) Date: May 25, 2005

(87) PCT Pub. No.: WO03/072870

PCT Pub. Date: Sep. 4, 2003

(65) Prior Publication Data
US 2005/0251931 A1    Nov. 17, 2005

(30) Foreign Application Priority Data
Feb. 28, 2002   (DE) ................. 102 08 773

(51) Int. Cl.
C09B 67/34    (2006.01)
D06L 3/12     (2006.01)

(52) U.S. Cl. ............................. 8/573; 8/648
(58) Field of Classification Search ......... 8/573, 8/648
See application file for complete search history.

(56) References Cited

U.S. PATENT DOCUMENTS

| | | | |
|---|---|---|---|
| 3,131,079 A | 4/1964 | Wagner et al. |
| 3,135,742 A | 6/1964 | Wagner et al. |
| 3,560,485 A | 2/1971 | Schinzel et al. |
| 3,690,947 A | 9/1972 | Rosch et al. |
| 3,925,367 A | 12/1975 | Boehmke et al. |
| 4,129,563 A | 12/1978 | Patsch et al. |
| 4,164,500 A | 8/1979 | Patsch et al. |
| 4,183,851 A | 1/1980 | Patsch et al. |
| 4,183,853 A | 1/1980 | Schroeder et al. |
| 4,187,226 A | 2/1980 | Patsch et al. |

FOREIGN PATENT DOCUMENTS

| | | | |
|---|---|---|---|
| DE | 1155418 | | 10/1963 |
| DE | 1237124 | | 3/1967 |
| DE | 1904424 | | 8/1970 |
| DE | 2011552 | | 10/1971 |
| DE | 1469222 | | 3/1972 |
| DE | 2050725 | | 4/1972 |
| DE | 2248772 | | 4/1973 |
| DE | 2534180 | | 2/1977 |
| DE | 2700996 | | 7/1978 |
| DE | 3134942 | | 3/1983 |
| DE | 19546518 | A1 * | 6/1997 |
| EP | 0073996 | | 3/1983 |
| GB | 906960 | | 9/1962 |
| GB | 993055 | | 5/1965 |
| GB | 1360490 | | 7/1974 |
| GB | 1412003 | | 10/1975 |
| SU | 1509461 | A1 * | 9/1989 |

OTHER PUBLICATIONS

*Indicates CAS Abstract Attached.*
Polk et al. (abstract from Journal of Elastomers and Plastics, vol. 30, No. 1, 45-54 (1998).*
English Translation of PCT IPER for PCT/EP2003/001730, mailed Oct. 23, 2003.

* cited by examiner

*Primary Examiner*—Rebecca Anderson
*Assistant Examiner*—Jason M Nolan
(74) *Attorney, Agent, or Firm*—Tod A. Waldrop

(57) ABSTRACT

The claimed liquid formulations contain an organic acid and a branched mono- or di-alcohol. The addition of the alcohol improves the storage stability of the liquid formulations.

13 Claims, No Drawings

AQUEOUS LIQUID FORMULATIONS OF PYRAZOLINE BRIGHTENERS

It is known to use certain pyrazoline brighteners, which bear basic groups and are present in the form of their salts with lactic acid, for brightening acrylic fibers (DE 3 134 942). A commercially available aqueous liquid formulation of such a brightener contains lactic acid, formic acid and methoxypropanol as well as the brightener. However, this formulation is still in need of improvement with regard to its stability in storage. It is thus an object of the present invention to provide aqueous liquid formulations of pyrazoline brighteners that have improved stability in storage. It has now been found that this object is achieved when a branched mono- and di-alcohol is added to the formulation of this brightener type.

The invention accordingly provides aqueous liquid formulations of pyrazoline brighteners of the formula

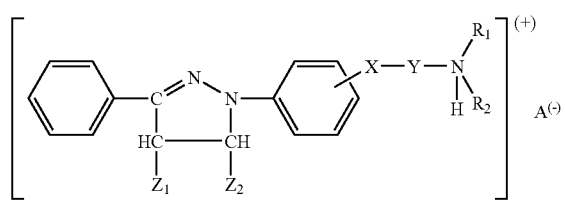

(I)

where
X is O, $SO_2$, $SO_2NZ$ or a direct bond,
Y is an alkylene chain which may be interrupted by O, S or CONH,
Z is H or alkyl,
$R_1$ and $R_2$ are singly an alkyl, cycloalkyl or aralkyl radical or together the remaining members of an N-heterocycle,
$Z_1$ is H or alkyl,
$Z_2$ is H, alkyl or aryl, and
A is an anion of an organic acid, wherein these liquid formulations contain an organic acid and a branched mono- or di-alcohol as well as a pyrazoline brightener of the above formula.

Suitable alkyl radicals $R_1$ and $R_3$ are especially those having 1 to 4 carbon atoms, which may be substituted by halogen such as fluorine, chlorine and bromine hydroxyl groups, cyano groups, $C_1$-$C_4$-alkoxy groups, phenoxy groups, $C_2$-$C_5$-alkylcarbonyloxy groups or $C_2$-$C_5$-alkoxycarbonyloxy groups.

Suitable cycloalkyl radicals $R_1$ and $R_2$ are cyclopentyl and cyclohexyl radicals.

Suitable aralkyl radicals $R_1$ and $R_2$ are especially benzyl and phenylethyl radicals.

Suitable heterocyclic radicals which can be formed by $R_1$ and $R_2$ combining with the nitrogen atom are for example pyrrolidine, piperidine, imidazole, morpholine and thiomorpholine radicals.

Suitable alkyl radicals Z, $Z_1$ and $Z_2$ are especially unsubstituted alkyl radicals having 1 to 4 carbon atoms.

Suitable aryl radicals $Z_2$ are in particular phenyl radicals, which may be substituted by one or more halogen atoms, $C_1$-$C_4$-alkyl groups, $C_1$-$C_4$-alkoxy groups, cyano groups, carboxylic ester groups and carboxamide groups.

Useful alkylene radicals Y are especially those having 2 to 4 carbon atoms such as

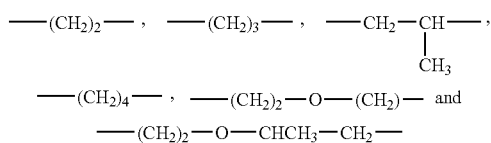

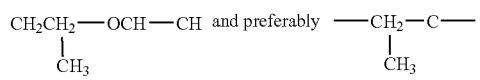

The anion $A^{(-)}$ may be an anion of a low molecular weight organic acid, examples being formate and lactate.

Preferred pyrazoline brighteners are those of the formula

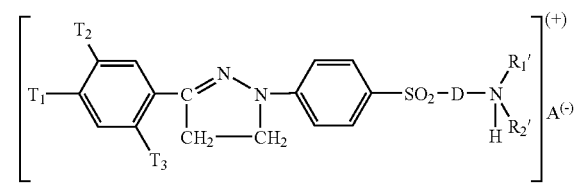

where
D is $-CH_2CH_2-$, $-CH_2CH_2CH_2-$, $-CH_2CH_2OCH_2CH_2-$, $-CH_2CH_2-OCH-CH-$ and preferably $-CH_2-C-$
           |                              |
           $CH_3$                         $CH_3$ $R_1'$ and $R_2'$ are each $C_1$-$C_2$-alkyl,
$T_1$, $T_2$, $T_3$ are H, $CH_3$ or Cl and
A is lactate or formate.

Preferably, $T_1$-$T_3$ do not represent Cl or $CH_3$ at one and the same time.

The amount of these pyrazoline brighteners in the ready-prepared liquid formulation can be 1% to 60% and preferably 5% to 30% by weight.

The pyrazoline bases which underlie the brightener salts defined above are known and are described for example directly or indirectly (as quaternary salts) in the following patent literature: DE-A 1 155 418, 1 237 124, 1 469 222, 1 904 424, 2 011 552, 2 050 725, 2 248 772, 2 534 180 and 2 700 996 and U.S. Pat. No. 3,131,079 and also 3 135 742. As well as the brightener salt, the liquid formulations of the invention additionally contain organic acids and branched mono- or di-alcohols. Useful organic acids include low molecular weight organic acids of the kind which are customary for salt formation of pyrazoline bases, for example formic acid, acetic acid or lactic acid or mixtures of such acids. The amount of these acids based on the ready-prepared liquid formulation is generally in the range from 20% to 60% and preferably from 30% to 50% by weight.

The fraction of branched mono- or di-alcohol in the ready-prepared liquid formulation can be 15% to 40% and preferably 20% to 30% by weight. Preferred mono- or di-alcohols are neopentylglycol and tertiary butanol.

In addition, the liquid formulations of the invention can contain the auxiliaries customary for optical brighteners, such as for example hydrotropic agents (urea for example), solution-stabilizing agents (ethylene glycol diacetate for example), preservatives, water-soluble cationic shading dyes, each in amounts of up to 10% by weight.

The liquid formulations of the invention are preferably prepared by adding the individual components of the formulation in the following order and mixing them in a suitable manner: organic acid, branched mono- or di-alcohol, brightener salt, water. Instead of the brightener salt it is also possible to start from the underlying base and to increase the amount of organic acid by the amount needed for salt formation.

The liquid formulations of the invention have an improved stability in storage compared with the hitherto customary commercial form. This improved storage stability shows itself in that the color coordinates of these formulations rise distinctly less on prolonged storage in particular.

The liquid formulations of the invention are used in a conventional manner for incorporation into spinning dopes for the production of polyacrylonitrite fibers in the so-called wet-spinning process or for brightening ready-prepared acrylic fibers in an exhaust process.

EXAMPLES

A liquid formulation was prepared by intensively mixing the following components at room temperature in this order: 40 g of lactic acid; 6 g of formic acid; 23.3 g of neopentylglycol (90% pure); 19.2 g of brightener (about 79% pure); 11.5 g of water. The brightener used has the formula

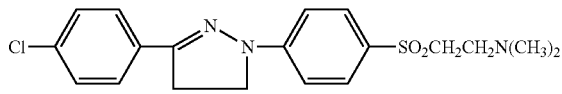

This liquid formulation was tested for storage stability (measurement of the color coordinates x and y) together with a commercially available liquid formulation of the same brightener. The commercially available liquid formulation contains 21 g of methoxypropanol and 13.8 g of water instead of 23.3 g of neopentylglycol and 11.5 g of water with the composition otherwise identical to that of the formulation of the invention.

The following x and y values were measured as a measure of stability for both formulations:

|  | Inventive formulation | | Commercial material | |
|---|---|---|---|---|
|  | x value | y value | x value | y value |
| At the start | 0.353 | 0.390 | 0.354 | 0.392 |
| After 4 weeks' storage RT/dark | 0.362 | 0.404 | 0.368 | 0.401 |
| After 4 weeks' storage 50° C./dark | 0.363 | 0.402 | 0.402 | 0.425 |
| After 10 weeks' storage RT/dark | 0.383 | 0.433 | 0.390 | 0.433 |
| After 10 weeks' storage 50° C./dark | 0.386 | 0.428 | 0.449 | 0.466 |

These values show that the color coordinates rise distinctly less for the formulation of the invention compared with the commercial material. This indicates superior stability for the inventive formulation, which contains neopentylglycol.

The invention claimed is:

1. An aqueous liquid formulation comprising an organic acid, a branched mono- or di-alcohol and a pyrazoline brightener of the formula

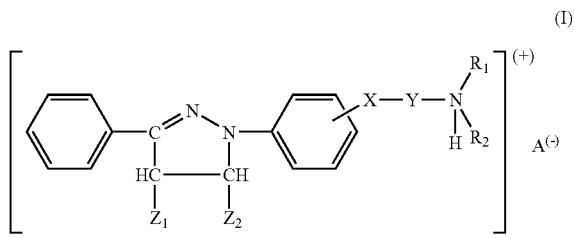

wherein
X is O, $SO_2$, $SO_2NZ$ or a direct bond,
Y is an alkylene chain,
Z is H or alkyl,
$R_1$ and $R_2$ are singly an alkyl, cycloalkyl or aralkyl radical or together the remaining members of an N-heterocycle,
$Z_1$ is H or alkyl,
$Z_2$ is H, alkyl or aryl, and
$A^{(-)}$ is an anion of an organic acid.

2. The aqueous liquid formulation comprising an organic acid, a branched mono- or di-alcohol, and a pyrazoline brightener compound of the formula

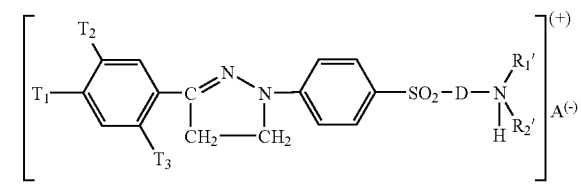

wherein
D is $-CH_2CH_2-$, $-CH_2CH_2CH_2-$, $-CH_2CH_2-OCH_2CH_2-$,

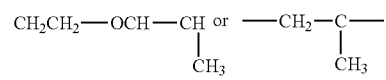

$R_1'$ and $R_2'$ are independently $C_1$-$C_2$-alkyl, $A^{(-)}$ is an anion of an organic acid, and
$T_1$, $T_2$, $T_3$ are independently H, $CH_3$ or Cl.

3. The aqueous liquid formulation according to claim 1, wherein the organic acid is lactic acid, formic acid, or acetic acid or mixtures thereof.

4. The aqueous liquid formulation according to claim 1, wherein the branched mono- or di-alcohol is neopentylglycol or tertiary butanol.

5. The aqueous liquid formulation according to claim 1, further comprising 20% to 60% by weight of the organic acid.

6. The aqueous liquid formulation according to claim 1, further comprising 15% to 40% by weight of the branched mono- or di-alcohol.

7. The aqueous liquid formulation according to claim 1, further comprising 1% to 60% by weight of the pyrazoline brightener.

8. The aqueous liquid formulation according to claim 1, further comprising at least one customary auxiliary.

9. The aqueous liquid formulation according to claim 1, wherein Y is an alkylene chain interrupted by O, S, CONH.

10. The aqueous liquid formulation according to claim 2, wherein D is

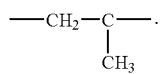

11. The aqueous formulation according to claim 2, wherein $A^{(-)}$ is lactate or formate.

12. A method for brightening an acrylic fiber comprising the step of incorporating an aqueous formulation according to claim 1 in the wet-spinning process or exhaust process for the acrylic fiber.

13. A method for brightening an acrylic fiber comprising the step of brightening the acrylic fiber with an aqueous formulation as claimed in claim 1.

* * * * *